United States Patent [19]
O'Reilly et al.

[11] 3,943,531
[45] Mar. 9, 1976

[54] APPARATUS AND METHOD FOR PRODUCING RING PATTERNS FROM ELECTRON DIFFRACTION SPOT PATTERNS

[75] Inventors: Dorothy F. O'Reilly, Claymont; James J. Byrd, Wilmington, both of Del.; Allan T. Finlayson, West Chester, Pa.

[73] Assignee: Sun Ventures, Inc., St. Davids, Pa.

[22] Filed: July 18, 1974

[21] Appl. No.: 489,626

[52] U.S. Cl. .................. 354/76; 354/75; 355/75; 96/27 R
[51] Int. Cl.² ................................ G03B 29/00
[58] Field of Search ........... 354/76, 75, 77, 78, 79, 354/80, 81, 4, 354; 355/75; 96/44, 27 R

[56] References Cited
UNITED STATES PATENTS

| | | | |
|---|---|---|---|
| 1,391,859 | 9/1921 | Schulze | 354/80 |
| 1,497,851 | 6/1924 | Hering | 355/75 |
| 3,008,372 | 11/1961 | Willey et al. | 354/80 |
| 3,148,085 | 9/1964 | Wiegmann | 96/44 X |

FOREIGN PATENTS OR APPLICATIONS

| | | | |
|---|---|---|---|
| 22,469 | 11/1906 | United Kingdom | 355/75 |
| 587,591 | 10/1933 | Germany | 96/27 R |
| 271,959 | 2/1951 | Switzerland | 96/27 R |

Primary Examiner—Robert P. Greiner
Attorney, Agent, or Firm—J. Edward Hess; Donald R. Johnson; Paul Lipsitz

[57] ABSTRACT

An apparatus for producing ring patterns from electron diffraction spot patterns, which comprises in combination a transparent disc rotatably mounted, rotating means for said disc, a light source beneath said disc, and photographic means above said disc. The invention also embodies a method for producing ring pattern negatives from an electron diffraction spot pattern negative by photographing the spot pattern negative while it revolves at a speed of at least about 0.5 rps.

1 Claim, 6 Drawing Figures

APPARATUS AND METHOD FOR PRODUCING RING PATTERNS FROM ELECTRON DIFFRACTION SPOT PATTERNS

In the field of x-ray diffraction methods, automatic equipment is available for measurement of the x-ray diffraction pattern, d-spacings and intensities. However, such equipment is not operable for an electron diffraction pattern because most patterns consist of spots rather than rings. It would, of course, be of great advantage and save much time if the spot electron diffraction patterns could be adapted for reading in the automatic reading equipment. It is accordingly an object of this invention to convert the spot patterns of electron diffraction techniques to ring patterns desirably without change in the relative intensities of the spots.

In accord with the invention, an apparatus is provided which comprises in combination, a transparent disc rotatably mounted, rotating means for said disc, said disc being between a light source and photographic means. The invention also provides a method for producing a ring pattern negative from an electron diffraction spot pattern negative which comprises photographing said spot pattern negative while it revolves at a speed of at least about 0.5 rps and then developing the exposed film.

In order to further illustrate the invention, reference is now made to the drawings.

Figure 1:
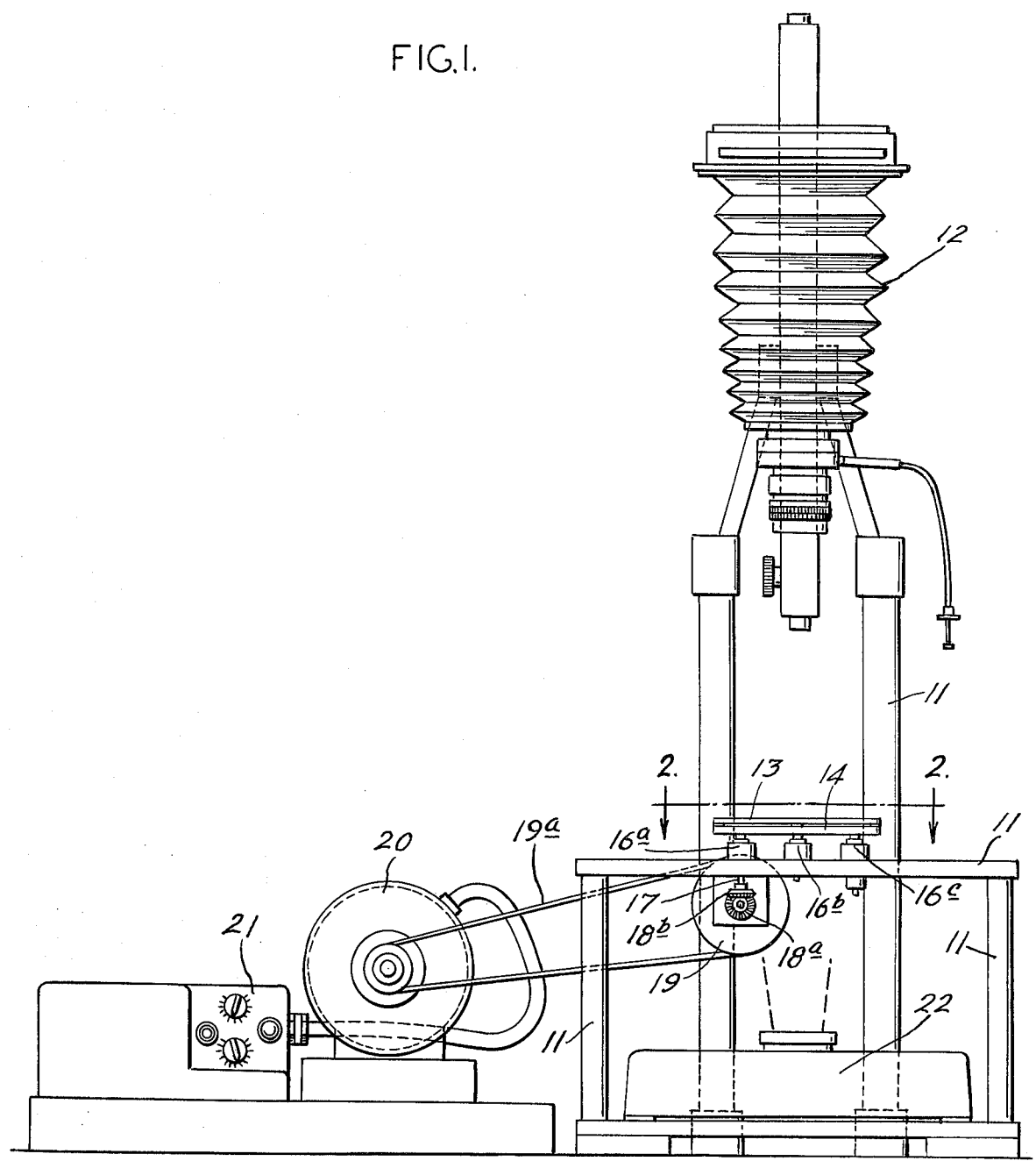
FIG. 1 is a front view of the complete apparatus.
Figure 2:
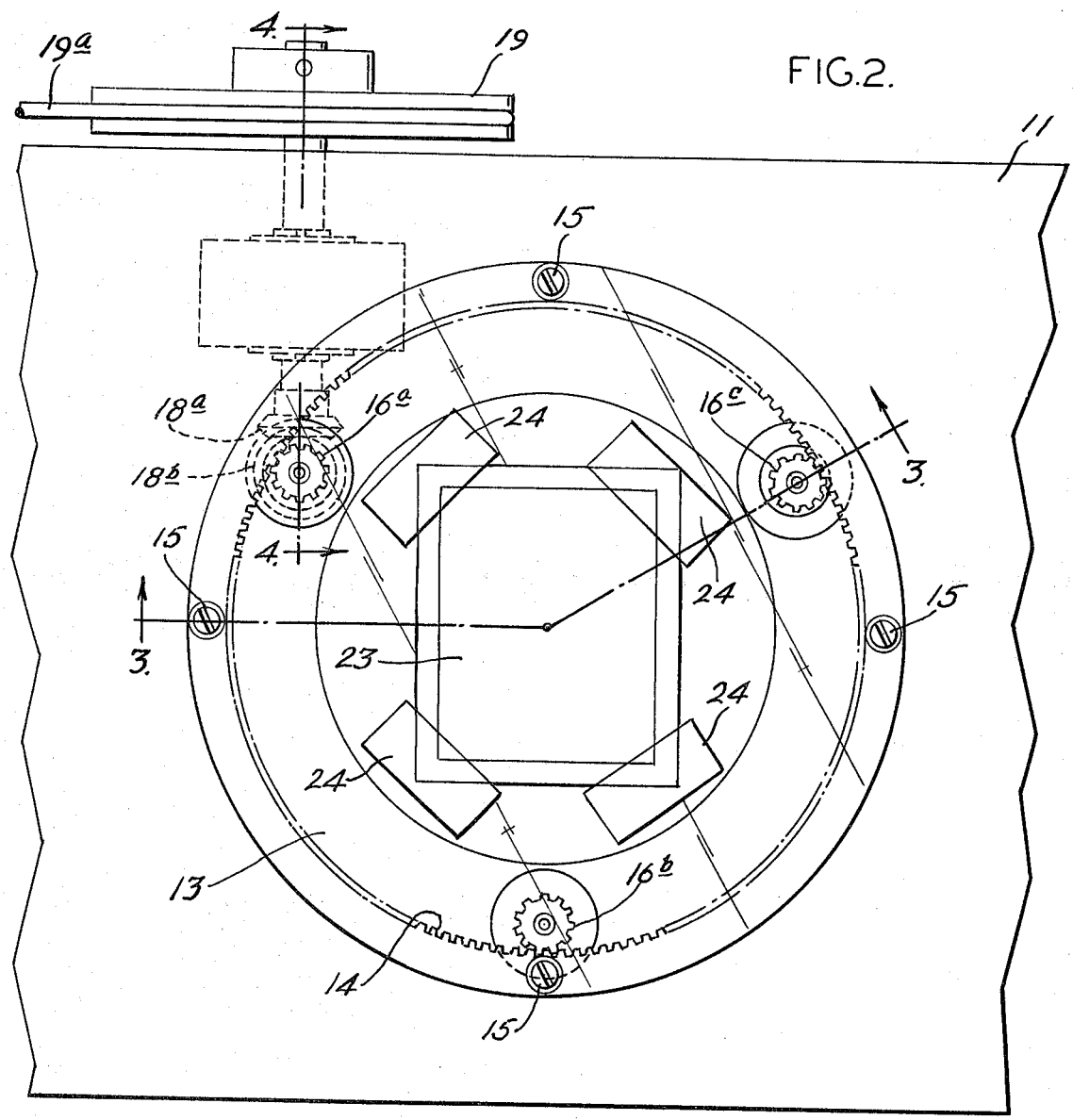
FIG. 2 is a top view taken on line 2—2 of FIG. 1.
Figure 3:
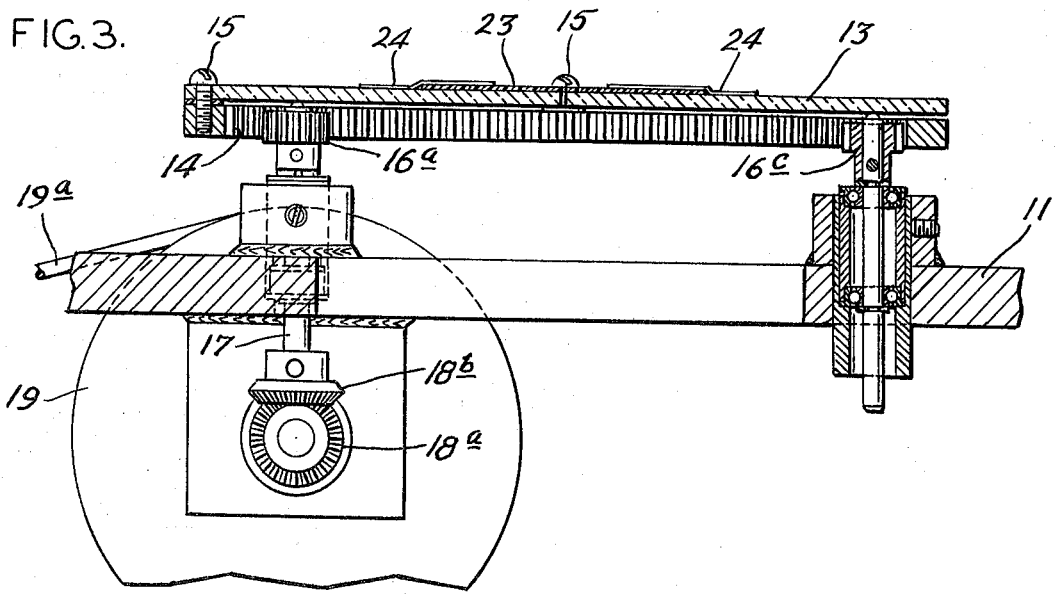
FIG. 3 is a view taken on line 3—3 of FIG. 2.

Referring now to FIGS. 1, 2 and 3, it is seen that the apparatus consists of a frame 11 supporting a camera 12 and a rotatable, transparent disc 13 mounted on a ring gear 14 by screws 15 (FIG. 2). The ring gear is mounted on three spur gear assemblies 16a, 16b, 16c one of which 16a is driven by means of a shaft 17 attached to a pair of bevel gears 18a and 18b driven by a pulley system 19 connected by a belt 19a to a motor 20. The speed of the motor can be changed as desired by a speed control 21 adjacent the motor. Within the frame 11 and below the disc 13 is a light source 22 for projecting a light beam upwardly through the transparent disc 13. It will be understood, of course, that, alternatively, the light source may be above the disc and the camera beneath it.

FIG. 2 shows a top view of the aparatus taken on line 2—2 and illustrates further the mounting of the transparent disc 13 as already described. As can be seen also, an electron diffraction negative 23 is mounted on the transparent disc 13 with pieces of an adhesive tape 24.

Figure 4:
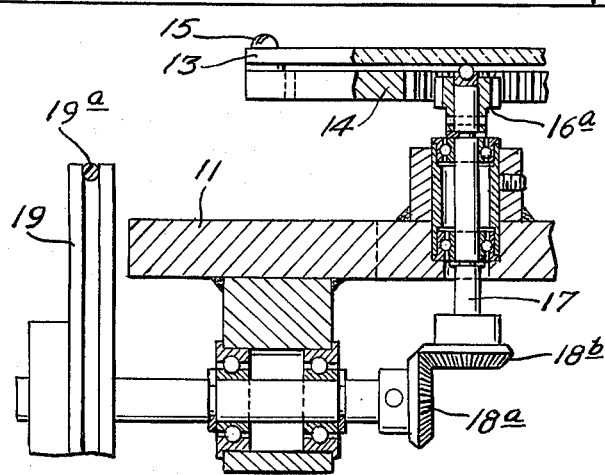
FIG. 4 is a view on line 4—4 of FIG. 3 and shows disc rotating means using bevel gears.

FIG. 3 is a side view along line 3—3 of FIG. 2 and gives further detail of the mounting and rotating means for the device. Likewise, FIG. 4 which is taken along line 4-4 of FIG. 2 shows in detail the pair of bevel gears 18a and 18b attached to a shaft 17 which is affixed to spur gear 16a and driven by the motor through pulley 19.

In carrying out the method of the invention, an electron diffraction pattern is obtained in the electron microscope using the standard selected area diffraction technique, taking two or more exposures. Multiple exposures are generally required because the spots cover a wide range of intensity values, and high d-values and strong spots might be lost in the increasingly blackened center portion or might be broadened before the weaker spots could be recorded. If inspection of the original photographs show high d-values and/or spots in one exposure which do not show in another, an intermediate negative is prepared from each exposure, unless direct positive films are used. The intermediate negatives are made by contact exposure of the originals and, in doing so, it is helpful to use a variable diaphragm inserted in the light path in order to burn in the darker central spot and reduce the overall contrast variations. The intermediate negative is then accurately centered on the transparent disc. This is accomplished by locating the center of the negative with a transparent template and piercing it with a sharp needle. With the needle still in the central hole, the negative is removed from the template and transferred to the transparent disc, the needle being pushed into a hole drilled into the disc center. The negative is then fastened firmly to the disc, usually with an adhesive tape, and the needle removed. The disc is then rotated and the negative exposed while such rotation takes place. Rotation should be at least about 0.3 rps and preferably will be from 0.3 to 3 rps, although higher speeds are, of course, operable. In developing the exposed film it is preferable to underdevelop about 25% in order to further reduce overall contrast. The developed film will show a ring pattern, which can be placed on a film densitometer to obtain d-values. It is to be understood, of course, that numerical relative intensity values, although obtainable from the densitometer charts, will be inaccurate due to exposure variables, but they may be found to be of some use in conjunction with ASTM card files.

Figure 5:
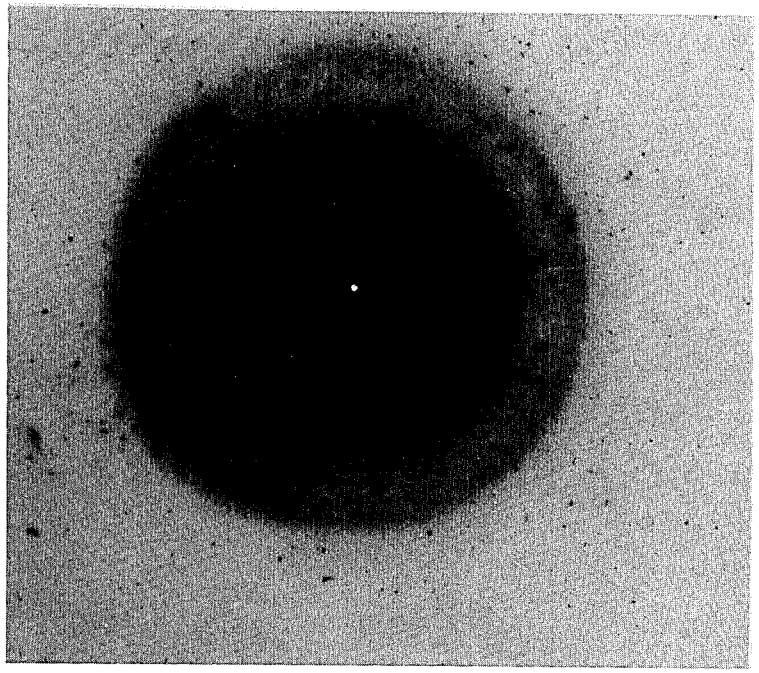
FIG. 5 illustrates an electron diffraction spot pattern as originally obtained.
Figure 6:
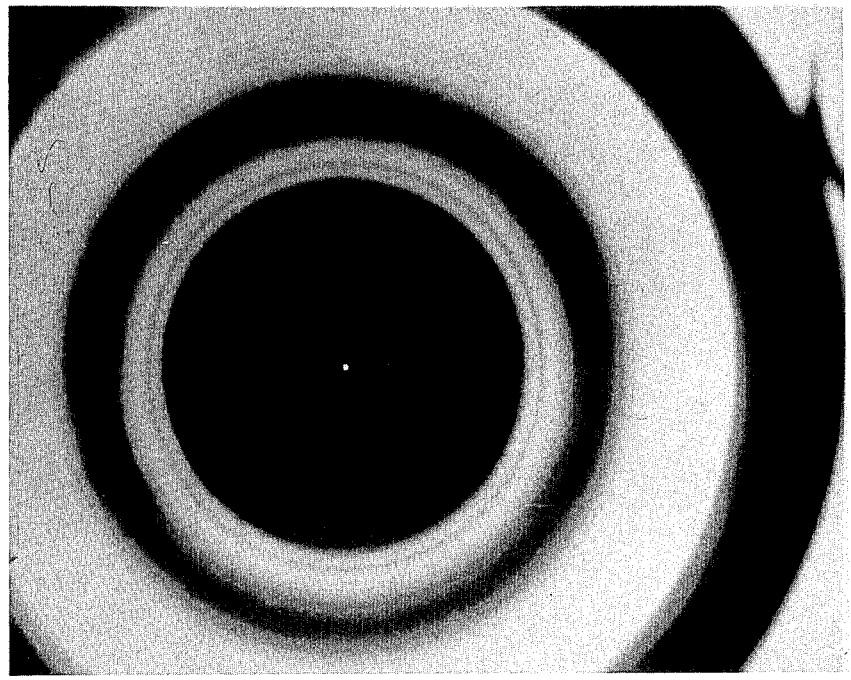
FIG. 6 illustrates the ring pattern obtained from the spot pattern using the invention.

Reference is now made to FIGS. 5 and 6 which illustrate the effect achieved by means of the invention. FIG. 5 photographically illustrates the diffraction pattern negative obtained from stannic oxide on an electron microscope. The dark spots scattered throughout the film represent the scattering of electrons due to the particular crystal spacings of the material under the microscope. A few rings do appear on the negative because the compound was impure and the rings result from completely random orientations of relatively high concentration of a component. In addition, the polymeric film substrate which supported the sample contributes some ring patterns, but these rings do not include the data represented by the scattered spots. FIG. 6 is a picture taken of the negative of FIG. 5 as it was spinning on the apparatus of the invention at 0.3 rps and it is clear that a series of distinct rings have been generated. These rings are adaptable to reading by the automatic reading equipment for x-ray diffraction patterns (e.g. a Siemens densitometer). Thus, it is clear that the invention provides a valuable contribution to the art.

The invention claimed is:

1. An apparatus for producing ring patterns from an electron diffraction spot pattern which comprises in combination, a frame supporting a rotatably mounted transparent disc having a center hole for centering an electron diffraction spot pattern negative on said disc, rim drive means for said disc, a light source mounted on said frame beneath said disc and directed upwardly at said disc, and photographic means mounted on said frame above said disc to photograph the ring pattern generated when said mounted spot pattern negative is revolved.

* * * * *